US008150522B2

(12) United States Patent
Echauz et al.

(10) Patent No.: US 8,150,522 B2
(45) Date of Patent: Apr. 3, 2012

(54) ACTIVE CONTROL OF EPILEPTIC SEIZURES AND DIAGNOSIS BASED ON CRITICAL SYSTEMS-LIKE BEHAVIOR

(75) Inventors: Javier R. Echauz, Alpharetta, GA (US); Gregory A. Worrell, Rochester, MN (US); Brian Litt, Bala Cynwyd, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 1257 days.

(21) Appl. No.: 11/505,906

(22) Filed: Aug. 18, 2006

(65) Prior Publication Data
US 2007/0043402 A1 Feb. 22, 2007

Related U.S. Application Data

(60) Provisional application No. 60/709,461, filed on Aug. 16, 2005.

(51) Int. Cl.
*A61N 1/18* (2006.01)
(52) U.S. Cl. .......... 607/45; 607/46; 607/47; 607/48
(58) Field of Classification Search .......... 607/2–3, 607/45–48, 115–116
See application file for complete search history.

(56) References Cited

U.S. PATENT DOCUMENTS

| | | | |
|---|---|---|---|
| 4,913,160 A | 4/1990 | John | |
| 5,391,147 A | 2/1995 | Imran et al. | |
| 5,843,093 A | 12/1998 | Howard, III | |
| 6,128,527 A | 10/2000 | Howard, III et al. | |
| 6,374,140 B1 | 4/2002 | Rise | |
| 6,495,601 B1 | 12/2002 | Hochman | |
| 6,560,486 B1 | 5/2003 | Osorio et al. | |
| 6,665,562 B2 * | 12/2003 | Gluckman et al. | 607/2 |
| 6,697,660 B1 | 2/2004 | Robinson | |
| 6,882,881 B1 | 4/2005 | Lesser et al. | |
| 6,887,239 B2 | 5/2005 | Elstrom et al. | |
| 2002/0091419 A1 * | 7/2002 | Firlik et al. | 607/45 |
| 2002/0117659 A1 | 8/2002 | Lieber et al. | |
| 2004/0019370 A1 * | 1/2004 | Gliner et al. | 607/48 |
| 2004/0133118 A1 | 7/2004 | Llinas | |

OTHER PUBLICATIONS

John Toon. "Merging Physics and Neuroscience: First Evidence of Self-Organized Criticality in Brain Networks". Georgia Institute of Technology Research News. Atlanta, Georgia. Date unknown.
Peter Jung. "Self Organized Criticality in Neuronal Assemblies". APS Mar. Meeting, Kansas City 1997. R21.06.
Gregory A. Worrell et al. "Evidence for Self-Organized Criticality in Human Epileptic Hippocampus". NeuroReport Lippincott Williams & Wilkins Nov. 15, 2002. vol. 13 No. 16.
PCT International Search Report and Written Opinion in counterpart International Application No. PCT/US06/32358, dated Oct. 30, 2007.

* cited by examiner

*Primary Examiner* — Niketa Patel
*Assistant Examiner* — Rex R Holmes
(74) *Attorney, Agent, or Firm* — Woodcock Washburn LLP

(57) ABSTRACT

Developing a measure of critical systems-like behavior in an epilepsy patient in order to map epileptic networks, either passively or evoking responses through subthreshold stimulation, and to apply "therapeutic" stimulations to the patient that cause smaller, but more frequent dissipations of "energy," a transcription product, subclinical electrophysiological activity or seizures in order to raise the clinical seizure initiation threshold, through releasing accumulated interictal energy in a seizure onset zone or elsewhere in the epileptic network, thereby preventing occurrence of larger more debilitating seizures.

26 Claims, 6 Drawing Sheets

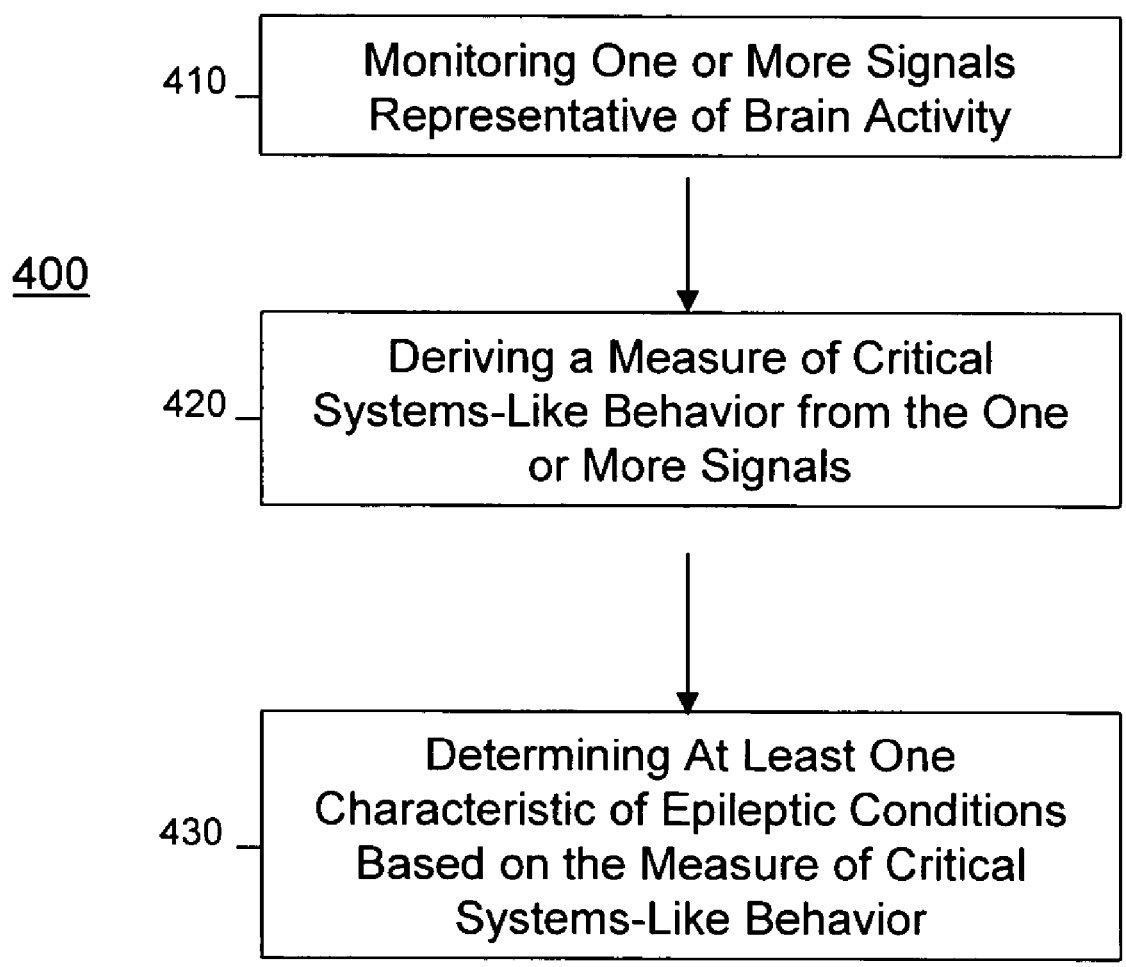

ACTIVE CONTROL OF EPILEPTIC SEIZURES AND DIAGNOSIS BASED ON CRITICAL SYSTEMS-LIKE BEHAVIOR

CROSS REFERENCE TO RELATED APPLICATIONS

This application claims priority to U.S. Provisional Application No. 60/709,461, filed Aug. 19, 2005, the entirety of which is incorporated herein by reference.

BACKGROUND OF THE INVENTION

The present invention relates to the field of medical devices to treat neurological disorders of the brain.

Complex dynamic systems that are open to energy/mass and/or information exchanges with their environment typically display emergent properties of self organization (SO)—patterns or behaviors ascribable to the collective ensemble but not particularly in the individual components. A class of SO behavior, termed self-organized criticality (SOC), can be sustained for certain ranges of system parameters in which energy fluctuations lose their characteristic amplitude and time scale, thus displaying self-similar events on a wide range of scales. In an SOC state, the system slowly accumulates some form of energy/mass and/or information that makes it prone to a fast "catastrophic" event. A small perturbation can be sufficient to start the event, which in turn can unleash a domino effect. Thus, the dramatic qualitative changes appear to come abruptly, can spread, and often occur in clusters. While this chain of events naturally seeks a more stable configuration, the "accumulating" variable is destabilizing and thus the cycle self-perpetuates. The critical state is globally attractive and robust: in a subcritical state there would be room for "tension" to build up towards the critical state, whereas in a supercritical state, a very large event would release tension back down to the critical state.

Because replicas of the above phenomenon exist at all amplitudes and time scales, a hallmark of SOC is a power-law distribution of frequency vs. the size of events (and event durations, and possibly inter-event intervals). The probability distribution P(E) of an event of size E follows the shape of $1/E^{\alpha}$, so that if one plots log(P(E)) vs. log(E), a straight line with slope-$\alpha$ results. Such plots have been displayed in disparate contexts as Zipf and Pareto distributions, but they arguably manifest a common trait of SOC in which a complex system yields frequent small events, rare big events, and an orderly distribution of everything in between. Examples are ubiquitous, including the spatial distribution of galaxies, the distribution of wealth in nations, the prices on commodities markets, the population of cities, the transient of blackouts in power grids, the magnitude and temporal statistics of earthquakes, the behavior of snow and granule avalanches, the spread of forest fires, the activity of volcanoes, the water volume and times of rainfall, the vortices of turbulent flow, the frequency of use of a few common words, and the number of visitors attracted to Web sites, ranked by popularity.

There is strong evidence that seizures in the human brain have similarities to and features in common with such critical systems-like behavior (e.g., systems behavior comparable to SOC). See G. A. Worrell, S. D. Cranstoun, B. Litt, and J. Echauz, "Evidence for Self-Organized Criticality in Human Epileptic Hippocampus," *NeuroReport*, vol. 13, no. 16, pp. 1-5, 2002. Any brain learns and therefore self-organizes. The epileptic brain, however, appears to self-organize in the critical state, with seizures, seizure-like bursts, sharp waves, and spikes being the obvious multiple-size energy-dissipating events describable by the SOC theory.

The evidence of these findings in clinical observations is well appreciated, but not well described. For example, it is well known that individuals with epilepsy often display a type of conservation of dissipated "energy" in seizures, roughly measured by the amount of brain involved, the duration and severity of the events. This characteristic of an individual's seizures is also measured roughly by quantities such as the severity×duration×frequency of seizures.

There are many factors that can alter these individual variables, such as alterations in seizure medications, changes in seizure precipitants, underlying medical condition, and other factors. When a change in one of these factors takes place, affecting something such as seizure frequency, there is often a compensatory change in another parameter, such as amount of brain involved (e.g. simple partial, vs. complex partial, vs. secondarily generalized, in the case of partial onset seizures), duration or severity. As an example, a change in medications may convert a patient with a stable pattern of 4 complex partial seizures per month into 1 generalized convulsive seizure during the same time period, of the duration and severity roughly, averaged over time, to dissipate the same "energy" as the 4 milder seizures. Similarly, a patient with intermittent convulsions might be converted into much more frequent simple partial events. In the case of primarily generalized seizures, it may be that generalized convulsive events may be transformed into much less frequent absence, myoclonic or much smaller events. Again, these are inexact phenomena, and the above examples are provided more to illustrate these relationships rather than to describe an exact mathematical property of epilepsy.

In computer models of locally-coupled integrate-and-fire oscillator networks, "avalanches" in the number of firing oscillators have been observed with a lack of characteristic size for a certain range of network and driving function parameters. In an investigation of the pathological energy fluctuations in hippocampi of 7 patients with medication-resistant temporal lobe epilepsy, it was found that the frequency of occurrence of discharges of size E scaled as $E^{-\delta}$, and the frequency of occurrence of periods of size T between events scaled as $T^{-\gamma}$, over a range a decade and a half or more in size. This finding is consistent with the electrographic occurrence of numerous small epileptiform events in a given patient, the clinical observation of less numerous severe or grand-mal seizures in the same patient, and the tendency for seizures to occur in flurries. Furthermore, it was found that the scaling behavior itself (as characterized, e.g., by the slope parameter in log-log axes) may drift from one "constant" during an interictal state, to another and into a loss of linearity during a preictal state (e.g., 1 hour before catastrophic ictus). Such changes in scaling exponent are also observed in the integrate-and-fire oscillators model as a function of system parameters. These results demonstrated the presence of SOC-like scaling over a range more than a decade wide in the human epileptic brain.

It is desirable to expand on these findings and provide ways to use a measure of critical systems-like behavior to manage seizures in a patient.

SUMMARY OF THE INVENTION

According to one aspect of the present invention, a system and method are provided for mitigating or managing seizures in an animal comprising monitoring one or more signals representative of brain activity; deriving a measure of critical systems-like behavior from the one or more signals; and determining at least one characteristic of epileptic conditions in the animal based on the measure of critical systems-like behavior for diagnostic or therapeutic purposes.

These techniques may be used to map epileptic networks, by passively recording brain activity or by actively stimulating and evoking bursts of energy through a variety of subthreshold stimulation paradigms and recording brain activity, to determine locations to place sensing and/or stimulation electrodes as well as to minimize and guide epilepsy (resective and other) surgical procedures. In addition, these techniques may be used as an afferent portion of any therapeutic antiepileptic device or system, as well as part of a therapeutic modality, to apply stimulations to the patient that cause smaller, but more frequent dissipations of "energy", a transcription product, subclinical electrophysiological activity or seizures in order to raise the clinical seizure initiation threshold, through release of accumulated interictal energy in a seizure onset zone or elsewhere in the epileptic network, thereby preventing occurrence of larger more debilitating seizures.

Thus, the present invention provides for a system and method for diagnosing and/or treating epilepsy in an animal, comprising: monitoring one or more signals of brain activity in the animal; generating a measure of critical systems-like behavior from the one or more signals; and determining a diagnosis or parameters of a therapy to be administered based on said measure of critical systems-like behavior.

BRIEF DESCRIPTION OF THE DRAWINGS

FIG. 6 is a flow chart generally depicting methods according to the embodiments of the present invention.

DETAILED DESCRIPTION

Figure 1:
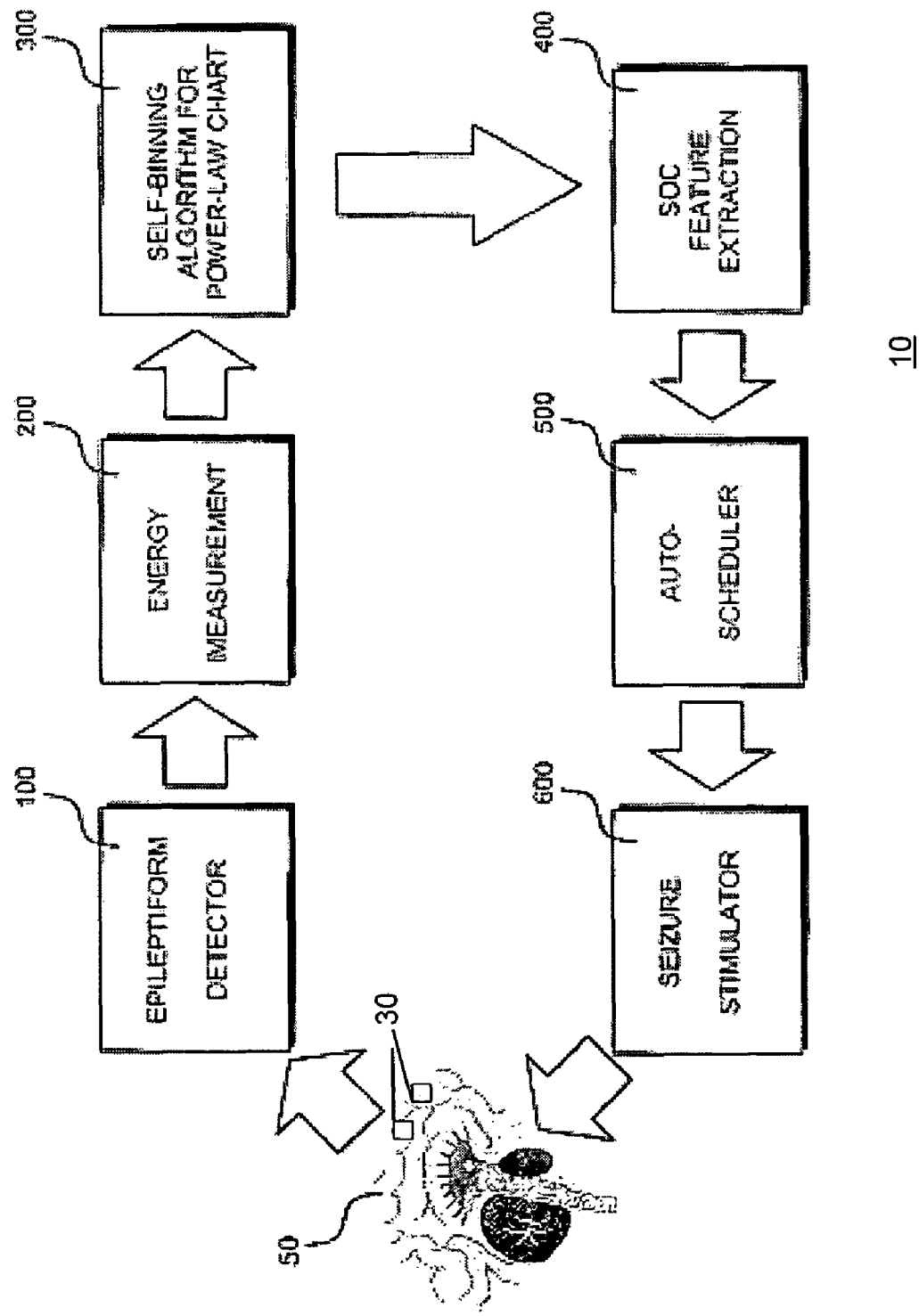
FIG. 1 illustrates a block diagram of an active seizure control system based on critical systems-like behavior in one mode of operation, according to an embodiment of the invention.

As used herein, the term "measure of critical system-like behavior" means a measure of the behavior of a system that has a critical point as an attractor, comparable and very similar to SOC behavior.

As used herein, the term "animal" means a human or non-human animal.

The basic premise of the systems and methods described below is that by exploiting this critical systems-like behavior of epileptic networks, it is possible to create strategies that minimize disability from epilepsy, as well as the severity and life-disruption of seizures. Such strategies may include causing brief, subclinical or completely asymptomatic epileptic events that occur frequently, perhaps precipitated by brain stimulation, which prevent larger, symptomatic events from occurring. It is also possible, in this scheme, that clinical events can be turned purely into electrographic events, with no clinical impact. There is significant evidence in the literature that critical systems behavior may be present in human epilepsy. For example, there are reports that stimulation preseizure, triggered by "chirps," or subclinical seizure-like oscillations, can prevent clinical seizure onset in patients with temporal lobe epilepsy, but that many, perhaps hundreds, of such stimulations may be necessary in order to dissipate adequate "energy" to have this effect, similar to generating multiple small avalanches to avoid a single large one. It is also reported that in the face of continued, responsive antiepileptic stimulation, the brain may generate many more pre-ictal chirps than normal, dissipating energy that would otherwise result in clinical epileptic events. The goal is to raise the clinical seizure initiation threshold (seizure threshold) to make clinically significant epileptiform activity (seizures, bursts, etc. that affect patient function) less likely. In so doing, the patient's brain activity is made to be more stable and less seizure prone.

Several schemes are described herein that exploit these system properties in order to disrupt and dissipate built-up energy in epileptic networks to modulate, prevent or minimize effects of clinical seizures, in a manner similar to periodically exploding the snow off avalanche prone mountains to prevent large, life-threatening events. These techniques have diagnostic applications such as by passively analyzing (spontaneous activity) signals at various brain regions/sites, or actively by stimulating the brain and recording evoked responses of different types. The spontaneous activity and/or evoked responses can be used to identify and locate critical regions in the epileptic network for purposes of one or more of: determining where to intervene (surgically); determining where to place recording/mapping electrodes; determining where to place device electrodes; and determining optimal locations for stimulation to modulate seizures.

According to one aspect of the present invention, techniques are provided that teach away from prophylaxis (open-loop antiepileptics, e.g., pharmacotherapy, vagal nerve stimulation, chronic or scheduled direct brain stimulation, surgical ablation, periodic cooling of the brain/neck), as well as from stoppage of individual seizures (closed-loop antiepileptics, e.g., responsive neurostimulation, responsive cooling of the brain). Directly blocking seizures can bring about paradoxical responses because energy dissipation may not be properly channeled. For example, repeated seizure interruptions by trigeminal nerve stimulation in experimental rats have been observed to be followed by a large breakthrough seizure upon cessation of the stimulation. Similarly, anecdotal reports of stimulation to abort brief pre-seizure, subclinical chirps, have resulted in the brain generating more abnormal, pre-ictal bursts than usual, requiring repeated stimulation to suppress seizures.

Patients treated with antiepileptic drugs frequently describe a somewhat similar situation, in which seizures may be transformed from infrequent severe events (prolonged, generalized convulsive seizures) into more frequent lower amplitude events (e.g. shorter complex partial seizures).

Thus, according to one aspect of the present invention, a pro-epileptic electrical or equivalent (other) stimulation is used in a temporally macroscopic closed loop to manage the ebb and flow of seizures. Rather than blindly attempt to abolish the critical systems-like behavior, a technique is provided for monitoring and modulating its scaling distribution using intentional, safely timed, small-seizure-provoking stimulations to release accumulated interictal energy in the seizure onset zone. The therapy is automatically adjusted using feedback of the power-law distribution to alter the measure of critical systems-like behavior in a direction that effectively trades off large seizures for more frequent, smaller, subclinical seizures (those with minimal or no symptoms to the patient). This change has a multiplying effect on quality of life since it is precisely the "large" clinically apparent seizures that devastate a patient's physical and psychosocial well-being.

The above concepts can be further understood in light of an avalanche analogy. Snow mass slowly accumulates on a hilly terrain. When bonds between crystals at a location are no longer strong enough to hold the weight of snow above, an avalanche is initiated. The shifting mass recruits neighboring snow on its way down certain preferred paths. Between any two avalanches, numerous smaller displacements will have taken place. Since the avalanche pathways tend to remain constant across events, experts can use targeted passive or active control techniques to prevent serious damage or injury. In passive avalanche control, defense structures such as earth mounds, dams, walls, and sheds are installed within the track and runout regions, or initiation-inhibiting structures such as fences, posts, and reforestation are located within the starting zone. These anti-avalanche measures are reactive (even if planted beforehand, actual counteraction starts when avalanche starts) and restrain damage allopathically. In marked contrast, active avalanche control consists of continuously managing risk by intently provoking more frequent, but smaller avalanches at controlled periods of time, when people can be cleared away to a safe distance. Stabilization is accomplished by explosives or ski-cutting (reshaping slope by skiing). These pro-avalanche measures are proactive and prevent damage homeopathically (principle of like-cures-like in small dose). The analogical relation of the foregoing example to active control of seizures based on a measure of critical systems-like behavior is summarized in the following table.

| Terrain | Neural Substrate |
|---|---|
| Accumulated snow | Accumulated interictal energy. |
| Avalanche | Clinical Seizure. |
| Smaller displacements | Seizure-like bursts, sharp waves, spikes/clusters, brief, localized, subclinical seizures, simple partial seizures that are well localized (in partial epilepsy). In primary generalized epilepsy these bursts might be brief generalized absences or subclinical bursts too short to cause overt clinical symptoms. |
| Starting zone | Ictal onset zone. |
| Track and runout regions | Spreading regions. |
| Preferred pathways | Stereotyped neuronal pathways in the epileptic network, in some instances created by adherent sprouting. |
| Defense structures: earth mounds, dams, walls, sheds | Drug serum level, VNS, chronic ANT stimulation, hemispherectomy, periodic cooling of the brain/neck, etc. |
| Initiation-inhibiting structures: fences, posts, reforestation | Local drug infusion, responsive neurostimulation, surgical resection of non-eloquent brain, etc. |
| Stabilization by explosives or ski-cutting | Stabilization by controlled seizure-provoking electrical stimulations. |

Thus, according to the above definitions, all heretofore known epilepsy remedies employ passive control (mostly reactive and allopathic), whereas the present inventive system allows for active control (proactive and homeopathic) according to one embodiment of the invention.

Referring first to FIG. 1, an active seizure control system according to an embodiment of the invention is shown at reference numeral 10. The system 10 comprises several components, labeled 200-600, that may be implemented by digital signal processing (DSP) techniques executed on one or more processors. These functional computation blocks may be implemented by software or firmware instructions executed by a processor. It should be understood, however, that these components may be implemented by one or more application specific integrated circuits (ASICs). Moreover, these components may be housed in the same package or in separate packages.

An epilepsy patient has one or more electrodes 30 surgically implanted in or near the seizure onset zone 50, or in areas of the epileptic network vital to seizure generation or its detection. The electrodes 30 can be macro, micro, or unit electrodes, or chemtrodes, microdialysis probes, optical detectors or other sensors that transduce seizure precursors, seizure onset or track seizure generation etc.

An epileptiform activity detector component 100 continuously monitors in real time intracranial EEG or other pertinent signals detected by the electrodes 30. It is known in the field that a seizure detector tuned to operate sensitively will generally produce "false positives" that are precisely the epileptiform events of interest for purposes of the present invention (e.g., spikes, sharp waves, seizure-like bursts, high-frequency epileptiform oscillations, in addition to seizures, and at the neural level: accumulation of particular proteins, substances, gene products, neuronal jitter, synchronization, and bursting), whereas it will specifically remain quiet during times of normal or background EEG. Thus, the epileptiform activity detector 100 can be embodied by any of the well-known seizure detectors. The detection of a pathological event automatically triggers a cascade of actions through components 200 to 600.

An energy measurement component 200 records the "size" of the detected event as a function of potentially disabling parameters:

"Size" of event=f(amplitude, frequency, duration, spatial extent), for example, size can be the total energy of the sampled EEG:

$$E = \Sigma_{channels\ k\ over\ spatial\ extent} \Sigma_{times\ i\ over\ duration\ of\ event} EEG^2[i,k].$$

Alternatively, since a high-amplitude/low-frequency event (such as delta waves during sleep stage 4) is benign compared to a high-amplitude/high-frequency event (such as certain seizures), the energy measurement can be implemented as nonlinear (Teager) energy $\Sigma EEG^2[i-1]-EEG[i]EEG[i-2]$, or as signal L1-norm variation (linelength) $\Sigma|EEG[i]-EEG[i-1]|$, to assign quadratic or linear weight emphasis, respectively, to frequency content.

It should be further understood that the variable that accumulates in the ictal onset zone, epileptic network, and/or elsewhere in the epileptic network or connected regions, is "energy" in a loose sense. In epilepsy patients, it is known that the time scales for how seizures change with intervention can be quite long: days, months, even years. Some of these time frames may represent conformational changes in synapses, accumulation of certain substances, neurotransmitter and ion channel expressions, gene products, proteins, membrane constituents, etc., all of which may qualify as accumulating variables. The conserved substance might also be a specific transcription product, or perhaps related to a cascade of products or substances. Thus, the energy measurement component 200 is not limited to the above standard EEG equations but may be based on concentration, temperature, pressure, entropy, enthalpy change, etc., and involve transducers at all bandwidths from DC to ultrahigh frequencies (kHz) and spatial resolutions down to gene expression and ion channel level.

A power-law charting component 300 "places" the energy size E calculated from 200 into one of Nb bins with exponentially increasing binwidths, thus representing a time-varying histogram of the energy distribution over the time since last reset, or a continuously refreshed histogram that covers a period of time, e.g., the most recent hour of EEG. In one embodiment, a "self-binning" algorithm exploiting the IEEE-754-standard binary representation of floating point numbers may be used for computational efficiency and suitability in an implantable or body wearable device. A single-precision number is represented as 32 bits $b_{32}b_{31}b_{30} \ldots b_3b_2b_1$, where $s=b_{32}$ is the sign (0=positive, 1=negative), the next 8 bits $e=b_{31}b_{30}b_{29}b_{28}b_{27}b_{26}b_{25}b_{24}$ are the biased exponent (=actual exponent+127), and the next 23 bits $f=b_{23} \ldots b_1$ are the fractional part of the normalized mantissa. Thus, the actual number stored in those 32 bits is $(-1)^s \times (1.f)_2 \times 2^{(e-127)}$, where $(1.f)_2$ converted to base 10 equals $(1+b_{23}2^{-1}+b_{22}2^{-2}+ \ldots +b_1 2^{-23})$. The histogram is a 256-element long array N[·] initialized to all zeros that will contain the bin counts. To update the histogram in real time, it may be advantageous to use low-level software to extract the biased exponent e from the energy value E calculated in 200, and use e directly as an index into the array N[e]. The base-2 logarithm of the array, log2N[e] (=powers of 2 for frequency of occurrence), plotted against e-127 (powers of 2 for size E), will have the same slope as the power-law in logP(E) vs. log(E), regardless of the log base. Since E "bins itself," this method avoids sorting or multiple logical comparisons which are computationally expensive in histogram routines. The same method is possible in double precision (64 bits) using an 11-bit exponent and a 1023 bias. The power-law charting component 300 produces a power-law chart or distribution having features that allow for characterizing the ongoing state of critical systems-like behavior in the patient.

With reference to FIGS. 2, 3 and 4(a) to 4(f), the SOC-like feature extraction component 400 extracts features of interest, such as a feature selected from a group of slope 310 of a least-squares straight-line fit of the data (possibly over a scaling region of 1.5 decades or about 5 octaves), the y-intercept 311 and x-intercept 312 of the line with respect to a set of reference axes defining a plot box and a quadrant 313 on the plane, and the centroid 314 of the line segment 315 within the plot box. The dynamic paths traced by these features over time provide a complete picture of whether therapy is improving the patient's condition, not achieving any improvement, or actually worsening the condition. Some patterns in these paths might require correlation with other electroencephalogram (EEG) parameters, or raw measures, in order to correlate them with improvement or progression toward seizure, in this setting.

As shown in FIG. 4(a), a therapy-off baseline period (a time period when no therapy is being applied) can be used to establish a reference or baseline state of critical systems-like behavior in the patient against which future comparisons are made. A power-law chart or distribution is created for the baseline state over a period of time, e.g., a 3-month period, under steady-state drug conditions, if any, but no electrical stimulation of seizures. A 95%-confidence envelope around the straight line may be obtained to assess variability over the course of sleep-wake cycles, interictal-to-preictal transitions, etc.

A rectangular plot box is defined to contain the largest region where scaling is still linear, and the reference y- and x-intercepts can be read off at the corners of the resulting axes. The reference centroid 314l is the midpoint of the line segment 315 within the plot box. The power-law line can rotate and drift over time; FIGS. 4(b)-4(f) show one neutral and four therapeutically beneficial routes of note during active control of seizures.

FIG. 4(b) shows the line rotating about the reference centroid 314. A completely vertical line would abolish critical systems-like behavior since there is a single characteristic size; however there is no net overall improvement since "medium"-size-only seizures occur.

FIG. 4(c) also shows slope magnitude increasing, y-int increasing, and x-int decreasing, but with simultaneous leftward movement of the centroid. This is the most common route to improvement according to an embodiment of the present invention, in which large seizures are effectively traded off for more frequent, smaller, subclinical bursts of synchronous neuronal activity. This change has a multiplying effect on quality of life since it is precisely the large (i.e., clinical) seizures that devastate a patient's physical and psychosocial well-being.

FIG. 4(d) shows slope magnitude increasing, with y-int constant, and x-int decreasing. This is a desirable route to improvement in which overall sizes of seizures are reduced.

FIG. 4(e) shows slope magnitude decreasing, with y-int decreasing, and x-int constant. This is a desirable route to improvement in which the overall frequency of seizures is reduced.

Finally, FIG. 4(f) shows simultaneous decrease in both intercepts. This is the most desirable route to improvement—one to seizure freedom—where the starred point 360 is equal to or nearly zero, thus seizures are eliminated. This can be the result of compounding therapeutic residual effects. In all cases, it can be seen that therapeutic benefit is achieved whenever the centroid of the power-law chart moves below the reference diagonal line segment 315 as shown in FIG. 4(f).

Referring back to FIG. 1, the auto-scheduler 500 is described. The auto-scheduler 500 incorporates macrotemporal feedback of the power-law distribution trajectory, e.g., in the form of a rulebase, to automatically adjust therapy. Schedule changes can include increasing the number of night-time small seizure (or other oscillatory energy) activations and/or parameters of the neurostimulation to alter critical-systems like behavior in a direction that pulls the centroid towards the lower triangle in the power-law chart. It is well known that electrical stimulation of the brain, for example, 50-Hz biphasic pulse trains during routine presurgical mapping of the brain, can elicit afterdischarges, runs of epileptiform activity seizure-like bursts, or seizures. A seizure stimulator component 600 coupled to the auto-scheduler 500 can employ such techniques to manipulate the number of small seizures (or other oscillatory energy) and thus alter the critical-systems like behavior characteristics as described above in connection with FIGS. 4(*a*) through 4(*f*) for purposes of applying a therapy to the animal based on the measure of the critical-systems like behavior.

Figure 2:
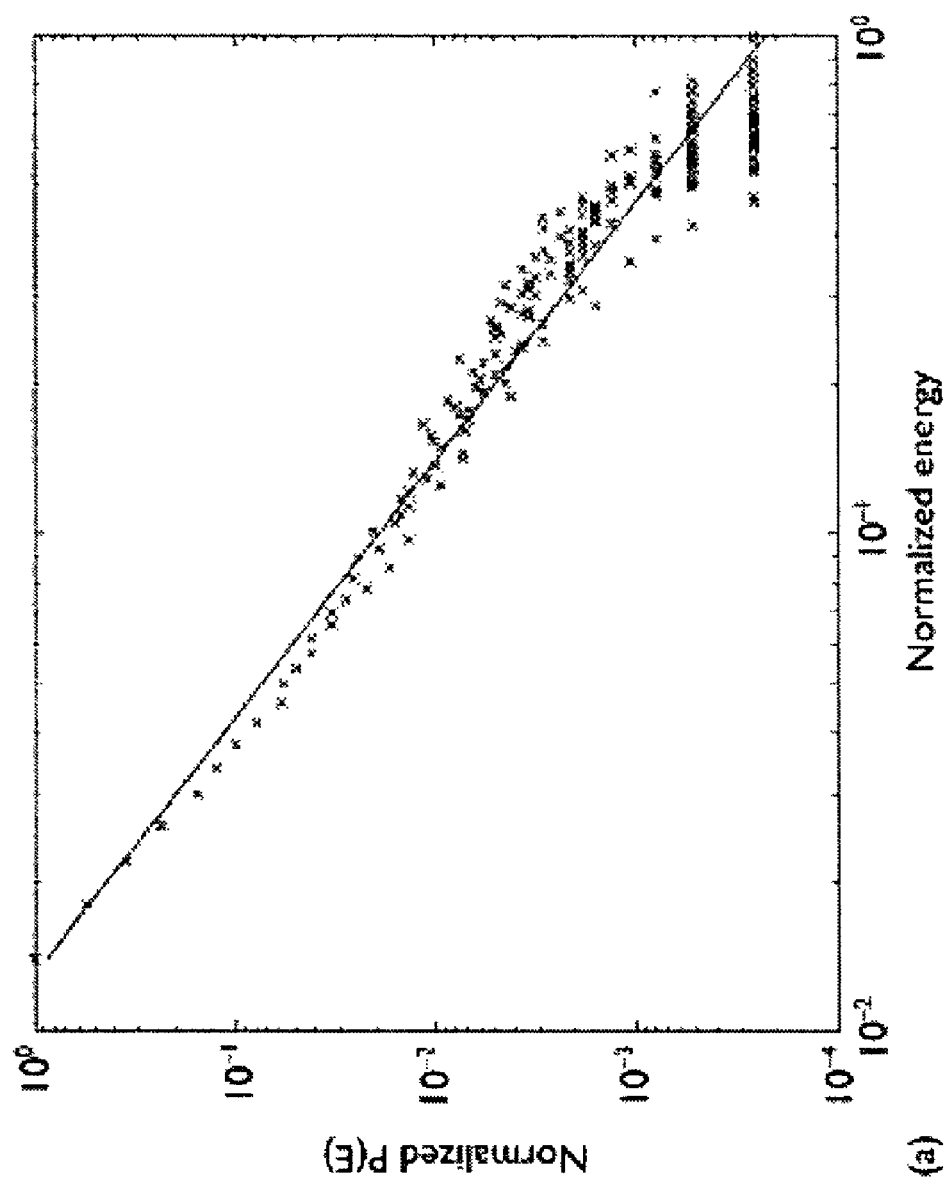
FIG. 2 illustrates a plot that shows the empirical distribution of interictal energy values bigger than threshold (1 standard deviation from average), obtained from continuously sliding 0.25-second long intracranial EEG windows in the seizure onset zone of a patient over an 8-hour recording, where the least-squares regression line has slope -1.9.
Figure 3:
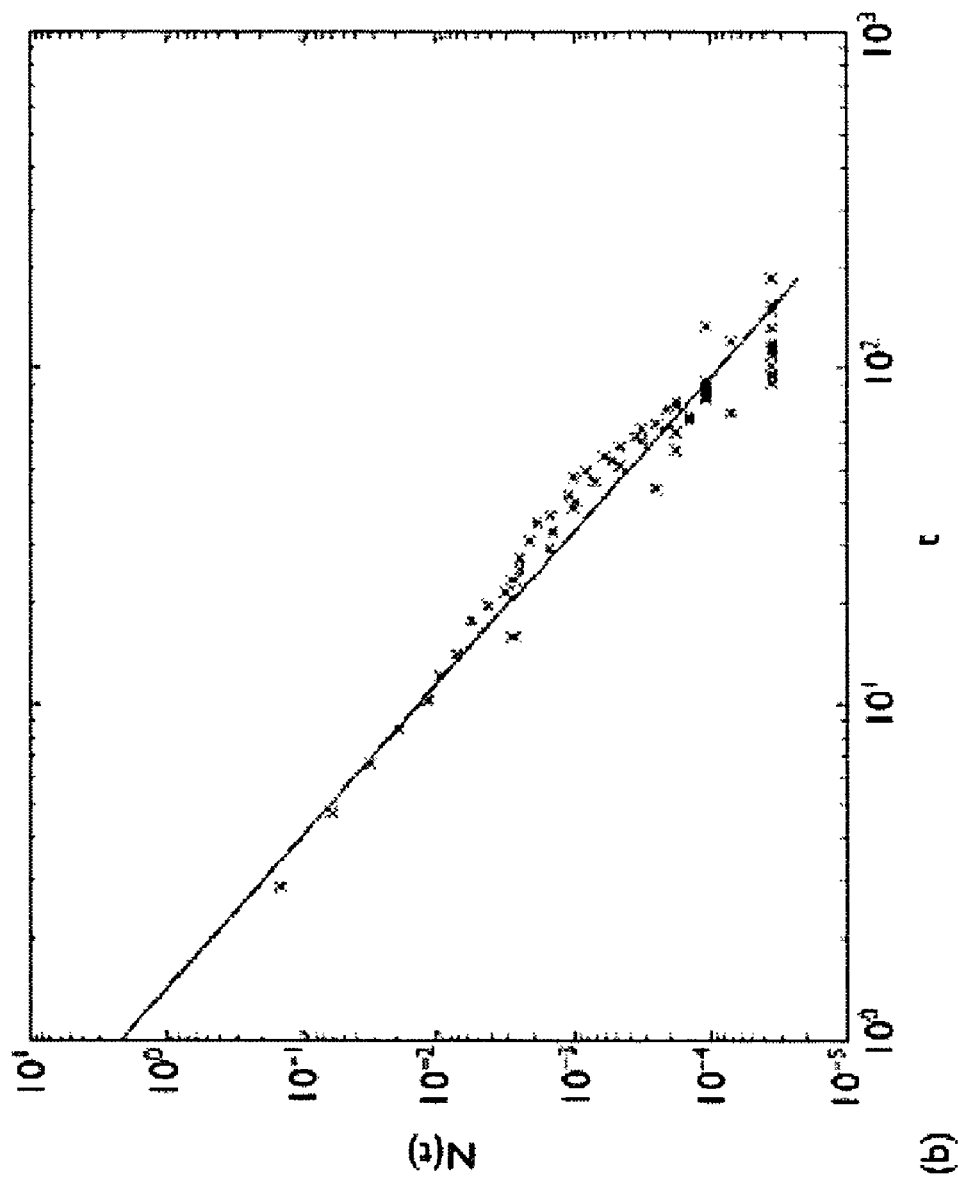
FIG. 3 illustrates a plot showing an empirical distribution of waiting times between consecutive energetic events larger than a threshold for the same 8-hour recording as shown in the plot of FIG. 2, where a least-squares regression line has slope-2.2.
Figure 4:
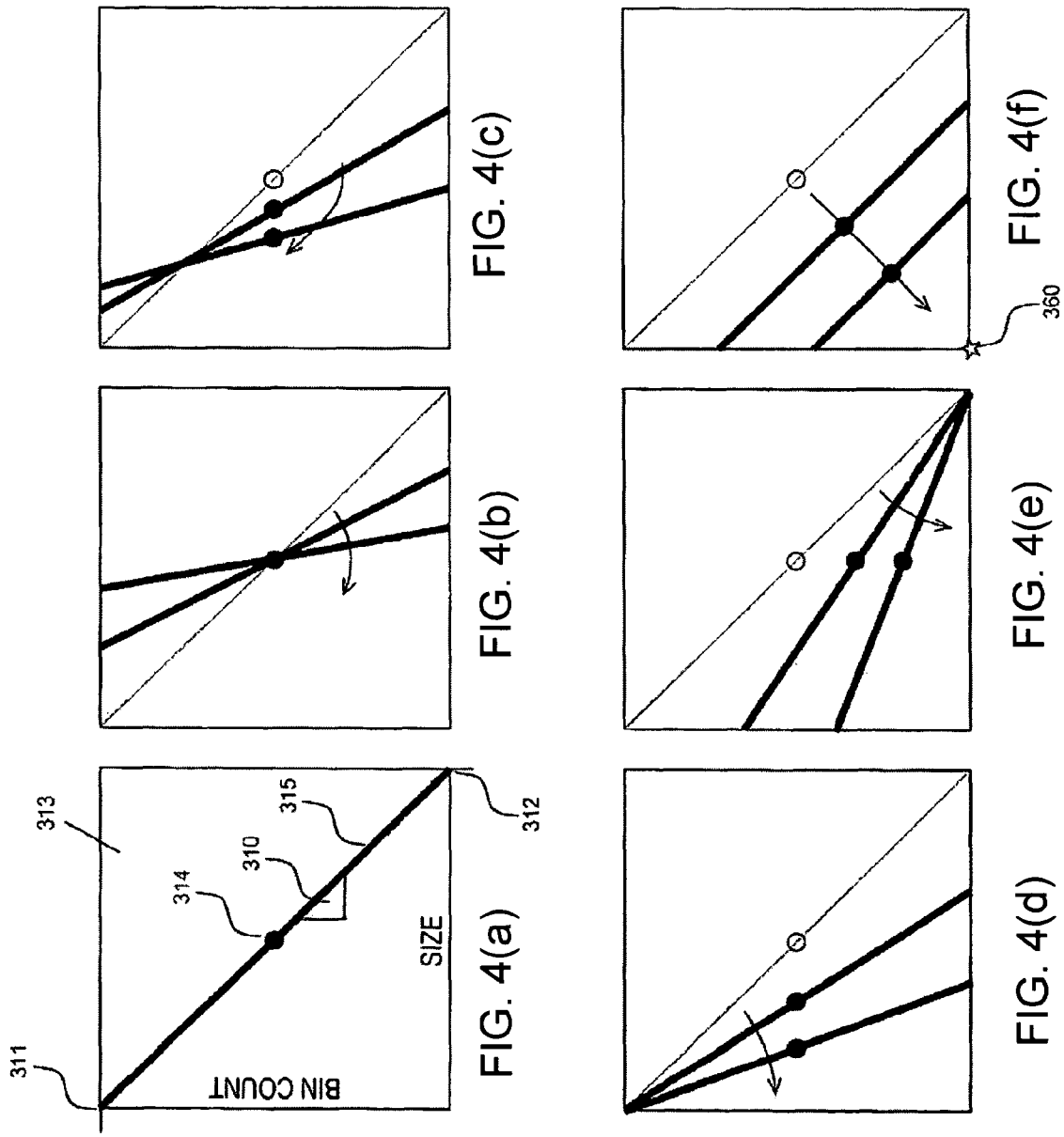
FIG. 4(a) illustrates a stylized power-law chart obtained during a 3-month therapy-off baseline period, information from which is used according to one embodiment of the invention.
FIG. 4(b) illustrates a stylized power-law chart showing a route to abolishment of critical systems-like behavior with no centroid leftward movement, thus no net improvement to the patient, according to an embodiment of the invention.
FIG. 4(c) illustrates a stylized power-law chart showing a route to improvement wherein large seizures are traded off for more frequent, smaller seizures according to an embodiment of the invention.
FIG. 4(d) is a stylized power-law chart showing a route to improvement wherein overall sizes of seizures are reduced according to an embodiment of the invention.
FIG. 4(e) is a stylized power-law chart showing a route to improvement wherein overall frequency of seizures is reduced according to an embodiment of the invention.
FIG. 4(f) is a stylized power-law chart showing a route to seizure freedom according to one embodiment of the invention.

Reference is now made to FIG. 6 for a description of a method 400 for mitigating or managing seizures in an animal employing the system 10 shown in FIG. 1 and the concepts represented by FIGS. 2, 3 and 4(*a*) through 4(*f*). The method 400 comprises at 410 monitoring one or more signals representative of brain activity through the use of various sensing electrodes 30 shown in FIG. 1. At 420, a measure of critical-systems like behavior is derived from the sensed one or more signals representative of brain activity. At 430, at least one characteristic of epileptic conditions in the animal is determined based on the measure of critical systems-like behavior, for diagnostic or therapeutic purposes. The diagnostic and therapeutic uses of the measure of critical systems-like behavior are described in more detail hereinafter. For example, one therapeutic application is to apply small stimulations to the animal based on the measure of critical systems-like behavior. The small stimulations release or dissipate accumulated interictal "energy" causing a modulation of a scaling distribution of the measure of critical systems-like behavior that raises the seizure threshold so as to make subsequent clinically significant epileptiform activity less likely. At 420, energy in the one or more signals may be measured to record a size of a detected brain activity event. Then, a time-varying histogram of energy distribution over a time interval is generated, from which a power-law chart or distribution is produced based on the energy size using the time-varying histogram. In one embodiment, at 420, the measure of critical systems-like behavior is determined by extracting and examining features of the power-law chart. Then, at 430, the small stimulations are adjusted based on the extracted features in order to alter the measure of critical systems-like behavior in such a manner so as to replace large seizures for more frequent smaller seizures.

Thus, one aspect of the present invention involves a method and apparatus to prevent large-energy seizures in an epileptic brain by controlling the size and frequency of small-energy seizures based on principles very similar to self-organized criticality. From a diagnostic perspective, the present invention has applications in mapping epileptic networks in an animal based on the measure of critical systems-like behavior in order to local regions of the brain more prone to clinical seizure activity, e.g., spatial localization of ictal onset zone, and temporal localization of preictal periods. The present invention also has applications to other bioelectrical phenomena, such as controlling and preventing cardiac dysrhythmias.

Figure 5:
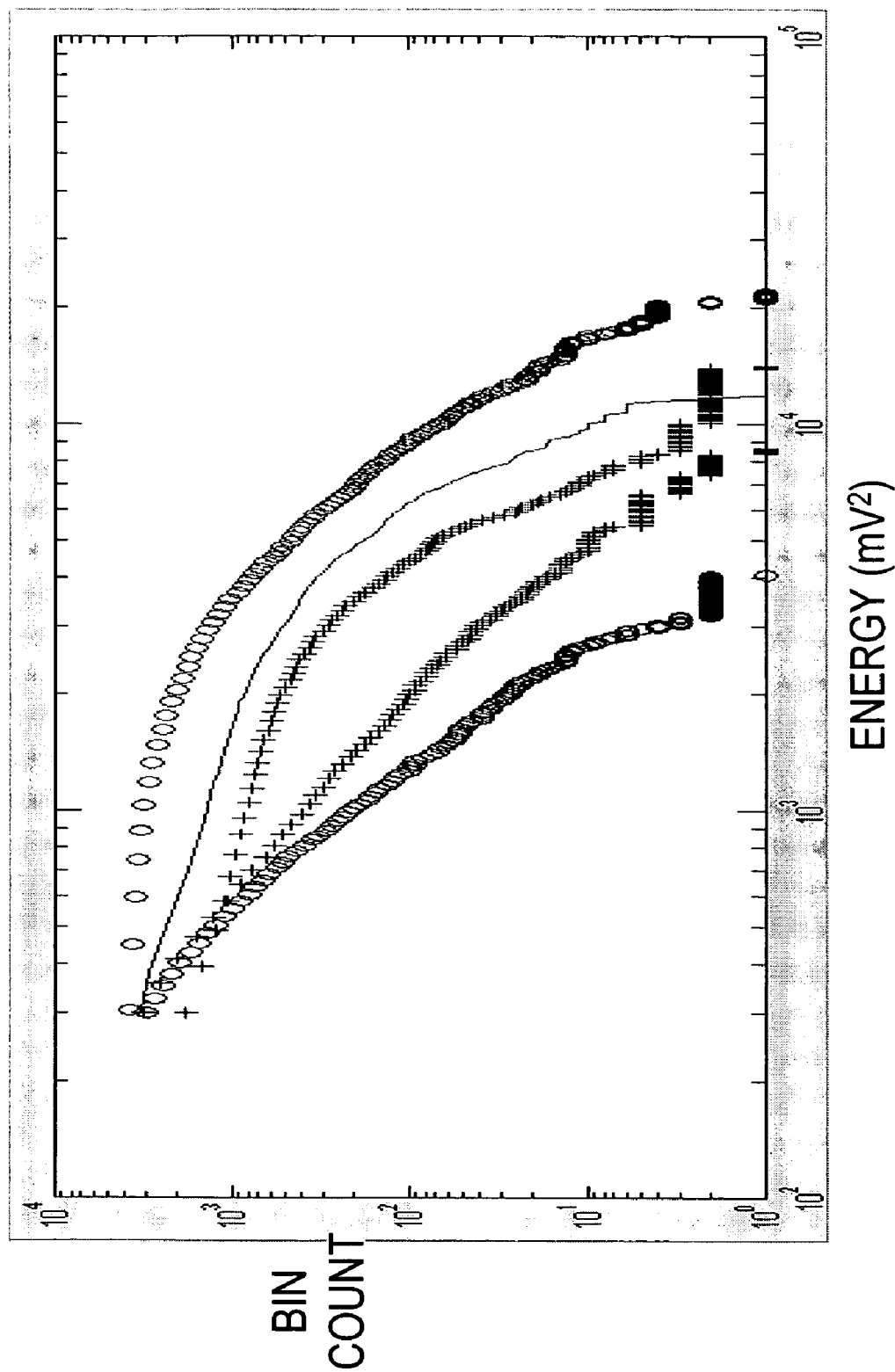
FIG. 5 is an overlay of 1-hour power-law charts for 2 interictal (blue) and 3 preseizure (red) records in a patient.

In an alternative embodiment of the invention, the epileptiform detector 100 is omitted. Because there is no way to distinguish discrete events in this case, an electro-encephalogram detector having a continuously sliding EEG window, such as with displacement overlap, is used as input to the energy measurement component 200. This creates more densely populated histograms that include many "normal" low-energy epochs. The power-law charts or distributions typically display a shallow-angle distribution from the left which then turns into a linear power law after a certain cutoff size. The smaller scales can correspond to "non-pathologic" fluctuations in size, as can be generated by purely random Poisson processes in normal EEG or the nonseizure state in an abnormal region. In that case, the lower end of the histogram abscissas (leftmost portion) corresponds to a shallow decay of an exponential rather than monomial (power function) distribution. The power-law distribution curve may be trimmed to include only events bigger than a certain threshold, so that a straight line is obtained in log-log axes as shown in FIGS. 2 and 3. The power-law line can drift and morph into an exponential-distribution curve that persists even after trimming, as shown in FIG. 5. Thus, according to still another aspect of the present invention, detection of an exponential-distribution curve in the power-law chart or distribution may be interpreted as a characteristic feature of an impending seizure.

In another alternative embodiment of the invention, the seizure stimulator 600 component is implemented as a heating element during the ictal onset zone. It is known that focal cooling of the brain has antiepileptic properties. It is believed that focal heating has a reverse effect wherein the seizure threshold is lowered and thus susceptibility to hypersynchronization of neural activity is increased as a function of temperature. Furthermore, studies suggest the relative increase in temperature required for heating to provoke epileptiform activity is an order of magnitude smaller than the relative decrease required for cooling to suppress such activity. Similarly, other locally delivered antiepileptics such as drug infusion, transcranial magnetic stimulation, etc., may have controllable reverse effects that can then be exploited by the techniques of the present invention. Thus, at 430, a therapy applied to the animal may comprise applying a treatment to the animal that has the effect of acutely lowering a seizure threshold to thereby increase a susceptibility of the animal to hypersynchronization of neural activity. The seizure threshold is momentarily manipulated to be low, but the overall chronic picture is one of increased seizure threshold/resistance to convulsions. Examples of such a therapy, as described above, are one or more of: heating an area of the brain of the animal to lower a seizure threshold; administering a drug to the animal; and performing transcranial magnetic stimulation.

The techniques of the present invention may also be deployed independent of an efferent limb, or intervention, but solely as a warning indication or for other diagnostic purposes. For example, at 430, the characteristic determined may be an identifier of pre-ictal periods, a map of the one or more epileptic networks in a patient and its subregions (seizure onset zone, epileptogenic zone, etc.). In addition, the measure of critical systems-like behavior may be used at 430 for determining one or more locations for implantation of sensing and/or therapeutic electrodes or devices. In one embodiment, mapping of epileptic networks is performed passively, that is based solely on monitoring the measure of critical systems-like behavior derived from the one or more signals. In another embodiment, a more active approach may be taken whereby small subthreshold stimulations are applied to the animal and the one or more signals are monitored (at 410) in response to the stimulations to record the evoked brain activity, from which the measure of critical systems-like behavior is derived to map the epileptic networks in the animal.

Whether mapped through passive or active techniques, such mapping information can be used for one or more of: determining connectivity among critical regions in the brain; determining locations for implantation of sensing, stimulating or other device electrodes; and minimizing and/or guiding epilepsy surgical (resective) procedures.

Online monitoring of the power-law distribution (components 100 through 400) provides additional uses. The first is as spatial locator of ictal onset zone, where the recorded channel exhibiting maximum range of power-law critical scaling is the ictal onset zone. The second is as temporal locator of preictal periods (seizure predictor), where the power-law curve drifts relative to its baseline condition, and its linearity is lost as shown in FIG. 5. Thus, according to still another embodiment, at 420, energy is measured in the one or more signals. Next, a time-varying histogram of energy distribution over a time interval is generated from the measured energy. A power-law chart or distribution is then generated at 420 based on energy size using the time-varying histogram. Finally, at 430, a characteristic of brain activity is determined from the power-law chart. For example, an ictal onset zone may be spatially located based on the power-law chart or preictal periods may be temporally located based on the power-law chart.

The system and methods described herein may be embodied in other specific forms without departing from the spirit or essential characteristics thereof. The foregoing embodiments are therefore to be considered in all respects illustrative and not meant to be limiting.

What is claimed is:

1. A method for mitigating or managing seizures in an animal, comprising:
    monitoring one or more signals representative of brain activity of the animal with at least one sensor;
    in at least one signal processing apparatus coupled to the at least one sensor, measuring energy in the at least one signal to record a size of energy for a detected brain activity event and generating a time-varying histogram of energy distribution over a time interval based on recorded energy size;
    in the at least one signal processing apparatus, determining whether the time-varying histogram of energy distribution is indicative of self-organized criticality behavior of the brain activity of the animal; and
    based on the self-organized criticality behavior, applying to the animal stimulations that are configured to dissipate energy thereby raising a seizure threshold so as to make subsequent clinically significant epileptiform activity in the animal less likely.

2. The method of claim 1, wherein determining comprises mapping epileptic networks in the animal based on the time-varying histogram of energy distribution in order to locate regions of the brain more prone to clinical seizure activity.

3. The method of claim 2, wherein applying stimulations comprises applying small subthreshold stimulations, and wherein monitoring comprises monitoring the one or more signals in response to said applying so that said mapping is based on evoked brain activity caused by said applying.

4. The method of claim 2, wherein determining comprises one or more of: determining connectivity among critical regions; determining locations for implantation of sensing, stimulating and/or other device electrodes; and
    minimizing and guiding epilepsy surgical procedures.

5. The method of claim 1, further comprising applying a treatment to the animal that has an effect of acutely lowering the seizure threshold to thereby increase a susceptibility of the animal to hypersynchronization of neural activity so as to cause an overall increase in the seizure threshold.

6. The method of claim 5, wherein applying a treatment comprises one or more of: heating an area of the brain of the animal to lower a seizure threshold; administering a drug to the animal; and performing transcranial magnetic stimulation.

7. The method of claim 1, wherein generating the time-varying histogram of energy distribution comprises assigning energy the size of a detected brain activity event into one of a plurality of bins with exponentially increasing binwidths.

8. The method of claim 7, wherein generating comprises generating a power-law distribution based on energy size from the time-varying histogram.

9. The method of claim 8, further comprising extracting features of the power-law distribution to generate a measure of the self-organized criticality behavior; and monitoring the measure of the self-organized criticality behavior.

10. The method of claim 9, wherein applying stimulations to the animal comprises applying stimulations that are configured to release accumulated interictal energy.

11. The method of claim 10, further comprising adjusting the stimulations based on the measure of critical systems-like behavior in such a manner so as to decrease the probability of clinical seizure.

12. The method of claim 11, wherein adjusting comprises adjusting the stimulations so as to achieve one or more of: replacing large seizures for more frequent smaller seizures, producing subclinical electroencephalogram bursts or releases of energy or of some transcription product that decreases the probability of a clinical seizure.

13. The method of claim 8, wherein determining comprises detecting an exponential-distribution curve in the power-law distribution as an indication of an impending seizure.

14. The method of claim 8, wherein determining comprises mapping the epileptic network or spatially locating an ictal onset zone based on the power-law distribution.

15. The method of claim 8, wherein determining comprises temporally locating preictal periods based on the power-law distribution.

16. The method of claim 9, wherein determining comprises identifying preictal periods based on the measure of self-organized criticality behavior.

17. A system for mitigating or managing seizures in an animal, comprising:
    at least one sensor that is configured to sense brain activity of the animal and to supply one or more signals representative of brain activity;
    a processor coupled to the sensor that measures energy in the one or more signals to record a size of energy for a detected brain activity event, generates a time-varying histogram of energy distribution of a time interval based on recorded energy size, determines whether the time-varying histogram of energy distribution is indicative of self-organized criticality behavior of the brain activity of the animal, and generates one or more controls based on the self-organized criticality behavior determined from the one or more signals; and
    a stimulating apparatus coupled to the processor and responsive to the controls from the processor, wherein the stimulating apparatus applies the animal stimulations that are configured to dissipate and thereby raise a seizure threshold to make subsequent clinically significant epileptiform activity in the animal less likely.

18. The system of claim 17, wherein the processor generates the time-varying histogram of energy distribution over a time interval by assigning the energy size of a detected brain activity event into one of a plurality of bins with exponentially increasing binwidths.

19. The system of claim 17, wherein the processor generates a power-law distribution based on the energy size using the time-varying histogram.

20. The system of claim 19, wherein the processor extracts features of the power-law distribution and monitors the measure of the self-organized criticality behavior.

21. The system of claim 20, wherein the processor generates the controls that are supplied to the stimulating apparatus to cause the stimulating apparatus to apply stimulations configured to release accumulated interictal energy.

22. The system of claim 21, wherein the processor generates the controls to adjust the stimulations applied by the stimulating apparatus based on the measure of the self-organized criticality behavior in such a manner so as to decrease the probability of clinical seizure.

23. The method of claim 9, and further comprising determining a diagnosis or parameters of a therapy to be administered to the animal based on said measure of the self-organized criticality behavior.

24. The system of claim 19, wherein the processor maps epileptic networks in the animal based on the measure of the self-organized organized criticality behavior in order to locate regions of the brain more prone to clinical seizure activity.

25. The system of claim 24, wherein the processor generates the controls to cause the stimulation apparatus to apply small subthreshold stimulations, and the processor monitors the one or more signals in response the application of the small subthreshold stimulations so that the mapped epileptic networks are based on evoked brain activity caused by the small subthreshold stimulations.

26. The system of claim 22, wherein the processor generates the controls to adjust the stimulations so as to achieve one or more of: replacing large seizures for more frequent smaller seizures, producing subclinical electroencephalogram bursts or releases of energy or of some transcription product that decreases the probability of a clinical seizure.

* * * * *

UNITED STATES PATENT AND TRADEMARK OFFICE
CERTIFICATE OF CORRECTION

| | | |
|---|---|---|
| PATENT NO. | : 8,150,522 B2 | Page 1 of 1 |
| APPLICATION NO. | : 11/505906 | |
| DATED | : April 3, 2012 | |
| INVENTOR(S) | : Javier R. Echauz et al. | |

It is certified that error appears in the above-identified patent and that said Letters Patent is hereby corrected as shown below:

<u>Title Page</u>,
Item (60), Related U.S. Application Data
Delete "Aug. 16, 2005." and insert -- Aug. 19, 2005. --.

Signed and Sealed this
Nineteenth Day of July, 2016

Michelle K. Lee
*Director of the United States Patent and Trademark Office*